United States Patent [19]
Gsell et al.

[11] Patent Number: 5,547,108
[45] Date of Patent: Aug. 20, 1996

[54] EXPRESSOR

[75] Inventors: Thomas C. Gsell; Frank R. Pascale, both of Glen Cove; Charles Lipari, Port Jefferson, all of N.Y.

[73] Assignee: Pall Corporation, East Hills, N.Y.

[21] Appl. No.: 284,268

[22] Filed: Aug. 2, 1904

Related U.S. Application Data

[63] Continuation of Ser. No. 156,643, Nov. 24, 1993, abandoned, which is a continuation of Ser. No. 912,731, Jul. 13, 1992, abandoned.

[51] Int. Cl.$^6$ .................................................. B65D 35/28
[52] U.S. Cl. ............................ 222/95; 222/105; 222/152; 604/140; 604/141; 604/146
[58] Field of Search ............................ 222/95, 105, 152, 222/183, 386.5; 604/131, 132, 133, 140, 141, 142, 146, 903

[56] References Cited

U.S. PATENT DOCUMENTS

| | | |
|---|---|---|
| 38,158 | 4/1863 | Ferris . |
| 2,579,092 | 12/1951 | Rockwell .................................. 72/24 |
| 2,757,375 | 7/1956 | Rieutord et al. ......................... 259/56 |
| 3,030,082 | 4/1962 | Matzen et al. ........................... 259/72 |
| 3,032,037 | 5/1962 | Huber ....................................... 604/133 |
| 3,577,579 | 5/1971 | Duve et al. ............................... 74/23 |
| 3,869,924 | 3/1975 | Beezer ...................................... 74/24 |
| 4,169,681 | 10/1979 | Kato ......................................... 366/244 |
| 4,601,213 | 7/1986 | Kimball ................................... 74/23 |
| 4,608,178 | 8/1986 | Johansson et al. ...................... 210/744 |
| 4,708,938 | 11/1987 | Hickinbotham ......................... 435/311 |
| 4,828,716 | 5/1989 | McEwen et al. ........................ 210/740 |
| 4,955,860 | 9/1990 | Ruano ...................................... 604/67 |
| 4,976,694 | 12/1990 | Schreibman ............................. 604/140 |
| 4,976,851 | 12/1990 | Tanokura et al. ....................... 210/86 |
| 5,035,865 | 7/1991 | Inaba et al. .............................. 422/99 |
| 5,045,185 | 9/1991 | Ohnaka et al. .......................... 210/86 |
| 5,057,429 | 10/1991 | Watanabe et al. ...................... 435/286 |
| 5,061,451 | 10/1991 | Gänshirt et al. ........................ 422/101 |
| 5,074,839 | 12/1991 | Choksi et al. ........................... 604/132 |
| 5,085,345 | 2/1992 | Wells ........................................ 222/95 |
| 5,102,407 | 4/1992 | Carmen et al. .......................... 604/410 |
| 5,141,490 | 8/1992 | Fujii et al. ............................... 604/6 |
| 5,147,330 | 9/1992 | Kogel ....................................... 604/903 |
| 5,207,645 | 5/1993 | Ross et al. ............................... 604/141 |

FOREIGN PATENT DOCUMENTS

| | | |
|---|---|---|
| 0446713 | 2/1991 | European Pat. Off. . |
| 51-3153 | 1/1976 | Japan . |
| 63-23644 | 1/1988 | Japan . |
| 1171612 | 11/1969 | United Kingdom ..................... 222/95 |
| 9207656 | 5/1992 | WIPO . |

*Primary Examiner*—Sherman Basinger
*Attorney, Agent, or Firm*—Leydig, Voit & Mayer

[57] ABSTRACT

An expressor for varying the amount of fluid in a variable-volume container connected to at least one conduit includes a housing defining an enclosed chamber which can accommodate the container. The housing has at least one opening through which a conduit can extend. A pressure regulating mechanism is coupled to the housing to vary the pressure of fluid in the chamber and thereby vary the volume of the container.

53 Claims, 7 Drawing Sheets

EXPRESSOR

This application is a continuation of application Ser. No. 08/156,643, filed Nov. 24, 1993, now abandoned, which is a continuation of prior application Ser. No. 07/912,731, filed Jul. 13, 1992, now abandoned.

FIELD OF THE INVENTION

The present invention relates to a system for expressing fluids from a fluid container, and more particularly to an apparatus for expressing fluids from a container using a pressurized housing.

BACKGROUND OF THE INVENTION

Whole blood is rarely administered to patients. Rather, patients needing red blood cells are given packed red cells (PRC), patients needing platelets are given platelet concentrate (PC), and patients needing plasma are given plasma. For this reason, the separation of blood into components has substantial therapeutic and monetary value.

The separation of a single unit of donated whole blood into its components is typically accomplished by use of differential sedimentation using centrifugation, as is well known to those skilled in the art. A typical procedure used in the United States utilizes a series of steps to separate donated blood into three components, each component having substantial therapeutic and monetary value. The procedure typically utilizes a blood collection bag which is integrally attached via flexible tubing to at least one, and preferably two or more, satellite bags. Using centrifugation, whole blood may be separated by differential sedimentation into such valuable blood components as plasma, packed red cells (PRC), platelet-rich plasma (PRP), and platelet concentrate (PC).

A typical blood processing procedure may include the following:

(1) The donated whole blood is collected from the donor's vein directly into the blood collection bag which contains a nutrient and anti-coagulant fluid.

(2) The blood collection bag, together with its satellite bags, are placed in a centrifuge bucket. The centrifuge bucket is then placed in the centrifuge. The centrifuge bucket, blood collection bag, and satellite bags are centrifuged together at a slow speed ("soft-spin" centrifugation). Red cells are heavier than other components of the blood. The centrifugal force of the centrifuge concentrates red cells as packed red cells (PRC) in a lower portion, i.e., the sediment layer, of the blood collection bag. The PRC fluid is bright red in color. The volume of the PRC fluid varies considerably depending on the number of red cells contained in the drawn whole blood (typically 37–54 percent by volume). A suspension of platelets in clear plasma, known as platelet-rich plasma (PRP) remains in the upper portion, i.e., the supernatant layer of the blood collection bag. The PRP fluid is light yellow in color. The interface between the supernatant PRP layer and the sediment PRC layer is known as the buffy coat interface. The location of the buffy coat interface can be determined by a visual inspection of the blood collection bag. This interface is seen as the point where the light yellow PRP fluid merges with the bright red PRC fluid.

(3) After centrifugation, the blood collection bag is transferred, with care not to disturb the buffy coat interface, into a device known as an expressor. A typical expressor is formed by a front and a back plate which are hinged together at their lower ends and spring biased toward each other. The blood collection bag is placed between the plates. The spring is released, and the plates are forced together, compressing the blood collection bag. A valve or clamp in the flexible tubing is opened, and the fluid is squeezed out of the blood collection bag by the expressor. The supernatant PRP layer is positioned at the top of the blood collection bag, and is therefore the first fluid to flow out of the collection bag. The supernatant PRP fluid flows into a first satellite bag.

An alternative means of expressing the fluid is a pressure cuff. The pressure cuff is constructed similar to a blood pressure cuff commonly used to determine a patient's blood pressure. The pressure cuff is wrapped around the blood collection bag. As the pressure cuff is inflated, the pressure cuff expands and bears against the collection bag, expressing the blood from the collection bag. Gravity may also be used to express the fluid from the blood collection bag.

As the PRP flows out of the blood collection bag, the buffy coat interface with the PRC rises. The operator closely observes the position of the buffy coat interface as it rises and clamps off the connecting tube when in his judgment as much PRP has been transferred as is possible, without allowing red cells to enter the first satellite bag. This is a labor intensive and time consuming operation during which the operator must visually monitor the bag and judiciously and arbitrarily ascertain when to shut-off the connecting tube.

The blood collection bag, now containing only PRC, may be detached and stored until required for transfusion into a patient. Alternatively, a valve or seal in the tubing may be opened so that the PRC may be transferred to a second satellite bag by means of the expressor.

(4) The PRP-containing satellite bag and another satellite bag are then removed from the expressor and centrifuged at an elevated G force (high speed or "hard-spin" centrifugation) with the time and speed adjusted so as to concentrate the platelets into the lower portion of the PRP bag. When centrifugation is complete, the PRP bag contains sediment platelet layer (light yellow in color) in its lower portion and supernatant clear plasma layer in its upper portion.

(5) The PRP bag is then placed in the expressor, and most of the clear plasma is expressed into a satellite bag, leaving the PRP bag containing only the sediment platelet layer and a small amount of residual plasma. In a subsequent step, the sedimented platelet fluid may be processed to make platelet concentrate (PC). The PRP bag, now containing a PC product, is then detached and stored until needed for a transfusion of platelets. For use with adult patients, the platelets from 4–8 donors may be pooled into a single platelet transfusion.

(6) The plasma in the satellite bag may itself be transfused into a patient, or the plasma may be separated by complex processes into a variety of valuable products.

In the above described procedures it is important to determine where the supernatant PRP fraction ends and the sediment PRC fraction begins. In separating the PRC and PRP fractions (e.g., step 3 above), blood bank personnel have attempted to ensure that the entire PRP fraction is recovered. This has often proved to be counterproductive since the PRP fraction may become contaminated by red cells from the buffy coat interface or the PRC fraction—giving a pink or red color to the normally light yellow PC. The presence of red cells in PC is so highly undesirable that pink or red PC is frequently discarded, or subjected to re-centrifugation, both of which increase operating costs and are labor intensive. As a result, blood bank personnel must err on the side of caution carefully observing the buffy coat interface and by stopping the flow of PRP before it has been fully expressed. Although the PRP is uncontaminated, valuable unexpressed plasma may be wasted.

Conventional expressors used in the above-described procedures have many drawbacks. For example, they apply an uneven pressure to the blood collection bag and may create wrinkles and folds in the bags. Blood products become trapped in these wrinkles and folds, preventing 100% of the fluid from being expressed. Uneven pressure also tends to disturb the buffy coat interface and reduce the amount of PRP which can be reliably collected. Additionally, because the bag may be distorted and because the structure of convention expressors can hinder observation of the container, it is very difficult to watch the buffy coat interface level to determine when to terminate the flow of the PRP fraction.

Further, in some applications, it is desirable to draw fluid into a container. For example, after a supernatant PRP layer has been expressed from a collection bag, it may be desirable to draw an additive solution into the collection bag and add it to the remaining PRC layer. However, conventional expressors are merely capable of squeezing a container. So while they can force fluid out of the container, they are unable to draw fluid into the container.

SUMMARY OF THE INVENTION

The object of the present invention is to alleviate the above-mentioned disadvantages by offering reliable, economical, and easy-to-operate mechanism for expressing fluid from a container such as a collection bag. Other objects of the invention include allowing for easy detection and observation of the buffy coat interface, minimizing the disturbance of the buffy coat interface as fluid is expressed from the container, applying an even pressure to the container, eliminating the formation of wrinkles and folds in the flexible bag while it is being expressed, maximizing the expression of fluid from the container and allowing fluid to be drawn into as well as forced out of the container.

Accordingly, the present invention provides an expressor for varying the amount of fluid in a variable-volume fluid container connected to at least one conduit. The expressor comprises a housing defining an enclosed chamber which can accommodate the container, the housing having at least one opening through which the conduit can extend, and a pressure regulating mechanism coupled to the housing to vary the pressure of a fluid in the chamber and thereby vary the volume of the fluid container.

The present invention may include a mechanism for oscillating the housing. Alternatively, the invention may include a hollow shaft utilized for imparting motion to the container and providing fluid communication to regulate pressure within the chamber. Further, the invention may include oscillating a container secured at first and second ends.

In preferred embodiments, the pressure regulating mechanism supplies and/or withdraws ambient air to and/or from the housing to vary the pressure on the fluid container within the chamber. If fluid is to be expressed from the fluid container, the pressure regulating mechanism increases the air pressure in the housing to a level above the pressure of the fluid in the container. If fluid is to be drawn into the fluid container, the pressure regulating mechanism decreases the air pressure in the housing to a level below the pressure of the fluid in the container.

DESCRIPTION OF THE PREFERRED EMBODIMENTS

An expressor embodying the invention may be used to facilitate the operation of many types of fluid processing systems. For example, the expressor may be coupled to one or more interconnected sterile blood collection bags and used to transport fluid from one bag to another. Alternatively, the expressor may be coupled to a bag containing a therapeutic or medical solution and be used to administer the solution to a patient via an administration set. In particular, the expressor may be used to process a biological fluid where biological fluid refers to any treated or untreated fluid associated with living organisms, especially blood, including whole blood, warm or cold blood, stored or fresh blood, treated blood, such as blood diluted with a physiological solution including saline, nutrient, and/or anticoagulant solutions, one or more blood components, such as PC, PRP, platelet-free plasma, platelet-poor plasma, plasma, PRC, or buffy coat, analogous blood products derived from blood or a blood component or from bone marrow, and similar biological fluids obtained by other means and with similar properties to the fluids described above.

Figure 1:
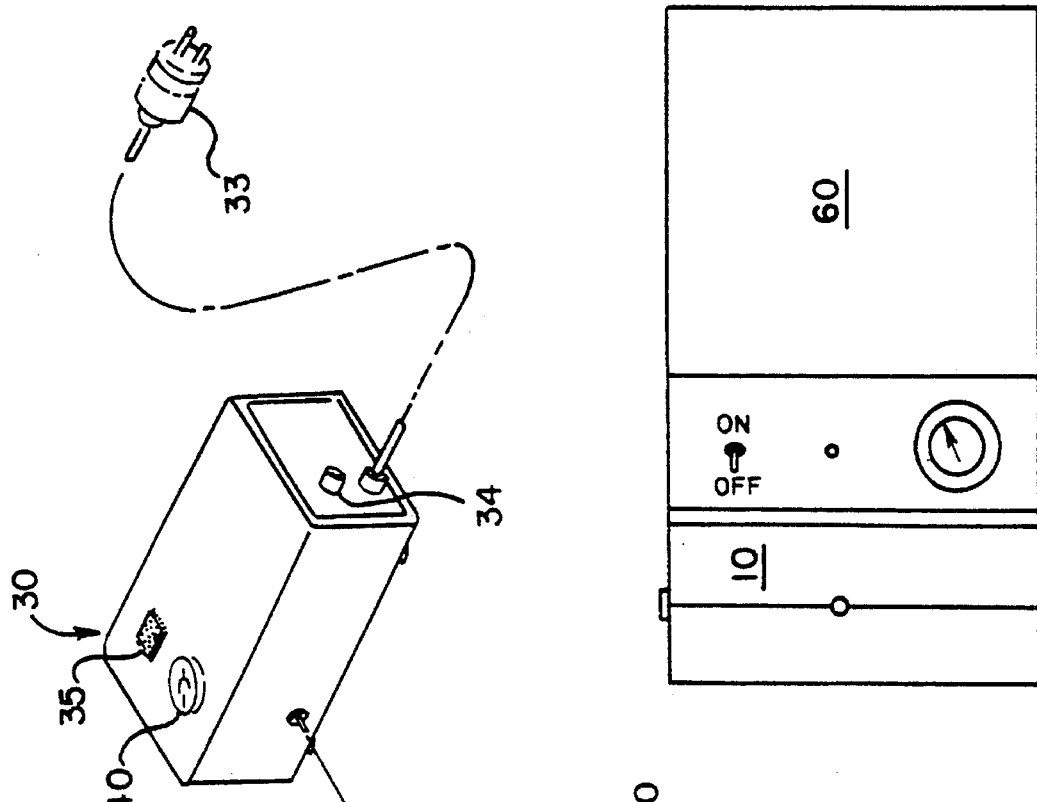
FIG. 1 is a perspective view of a first embodiment of an expressor according to the present invention.

As shown in FIG. 1, an exemplary expressor embodying the present invention comprises a housing 10 which defines an enclosed chamber 11 and a pressure regulating mechanism 30 coupled to the housing 10 by a flexible hose 31 or other conduit to vary the pressure within the chamber 11. A variable-volume fluid container 25, such as a flexible bag containing a biological fluid, may be placed in the chamber 11 with a conduit 26 extending from the fluid container 25 through an opening 17 in the housing 10 to the exterior of the housing 10. The fluid container 25 need not be flexible, but it preferably is constructed so that its internal volume can be varied by controlling the fluid pressure applied to the outside surface of the container 25. The pressure regulating mechanism 30 supplies and/or withdraws a fluid (i.e., either a gas or a liquid) to and/or from the chamber 11 in order to vary the pressure exerted on the container within the chamber 11. This, in turn, varies the volume of the fluid container 25 and thereby forces fluid (i.e., either a liquid or a gas) out of or into the fluid container 25 through the conduit 26.

The housing 10 may be formed from any suitable material which has sufficient structural integrity to withstand the differences in pressure between the chamber 11 and the exterior of the housing 10. The housing 10 may have a variety of configurations. For example, in the expressor shown in FIG. 1, the housing 10 is a parallelepiped and comprises a base 12 and a cover 13 which may be releasably mounted to the base 12 in any suitable manner to form the chamber 11 and envelop the container 25.

In the exemplary expressor, the cover 13 is releasably mounted to the base 12 by means of hinges 14 on one side of the base 12 and cover 13 and at least one and preferably two latches 15 on the other side. Although the latches may be configured in a variety of ways, they are preferably arranged to equalize the pressure between the chamber 11 and the exterior of the housing 10 before the cover 13 is completely released from the base 12. This prevents the cover 13 from suddenly and forcefully opening when the chamber 11 is at a higher pressure than the exterior of the housing 10.

Figure 2A:
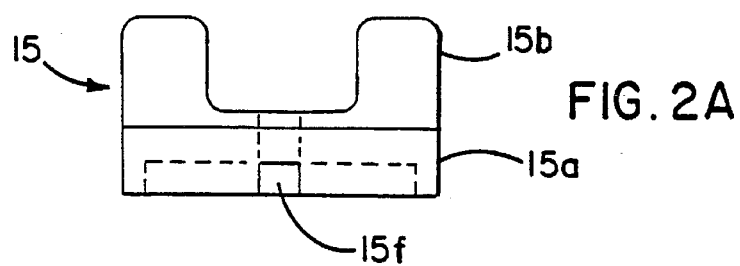
FIGS. 2A is a side view.
Figures 2B, 2C:
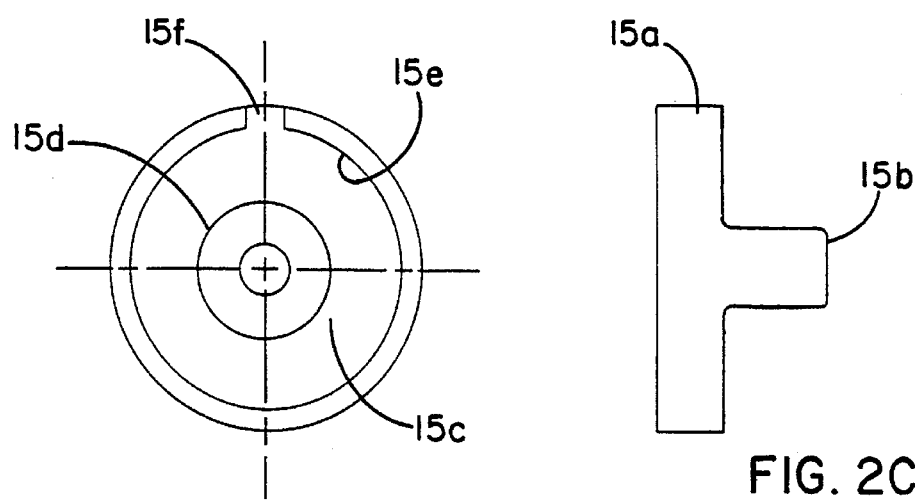
FIG. 2B is a bottom view.
FIG. 2C is a side view from another angle of a latch for the housing of the embodiment of FIG. 1.

In the embodiment of FIG. 1, each latch 15 is rotatably mounted on the base 12 and is designed to engage with a corresponding pin 16 mounted on the cover 13. FIGS. 2A–2C illustrate the structure of one of the latches 15 in detail. As shown in these figures, the latch 15 has a generally disk-shaped base 15a from the top surface of which extend lugs 15b by which the latch 15 can be grasped. As shown in FIG. 2B, the bottom surface of the base 15a has a track 15c formed therein for receiving a corresponding pin 16, the track 15c lying between an inner cam surface 15d and an outer cam surface 15e. A pin groove 15f is formed in the wall of the base 15a between the track 15c and the outside of the base 15a. The latch 15 may be biased, e.g., by a spring, so that the pin groove 15f is normally in position to receive the pin 16. Once the pin 16 enters the latch 15 through the pin groove 15f, it settles into the track 15c between the cam surfaces 15e and 15d. As the latch 15 is rotated to close the cover 13 on the base 12, the pin 16 rides along the outer cam surface 15e, which is eccentric to the center of rotation of the latch 15. This pulls the pin 16 toward the center of rotation and tightens the cover 13 against the base 12. A stop (not shown) may be provided, for example, 180° from the pin groove 15f, to lock the pin 16 in place once the cover 13 is properly sealed to the base 12.

To remove the cover 13 from the base 12, the latch 15 is again rotated. If the pressure within the chamber 11 is higher than the pressure exterior to the housing 10, the pin 16 will again ride along the outer cam surface 15e. This allows the pin 16 to move away from the center of rotation of the latch 15 while the pin 16 is maintained within the track 15c between the cam surfaces 15d and 15e. Thus, the cover 13 may separate somewhat from the base 12, equalizing the pressure in the chamber 11 and the pressure exterior to the housing 10, while the latch 15 remains engaged with the pin 16, preventing the cover 13 from flying open.

On the other hand, the pressure in the chamber 11 may be less than the pressure exterior to the housing 10. Then, as the latch 15 is rotated to open the cover 13, the pin 16 will ride in the track 15a along the inner cam surface 15d, which is also eccentric to the center of rotation of the latch 15. This forces the pin 16 away from the center of rotation, jacking the cover 13 off of the base 12 a distance sufficient to equalize the pressure in the chamber 11 and the pressure exterior to the housing 10.

Figure 7:
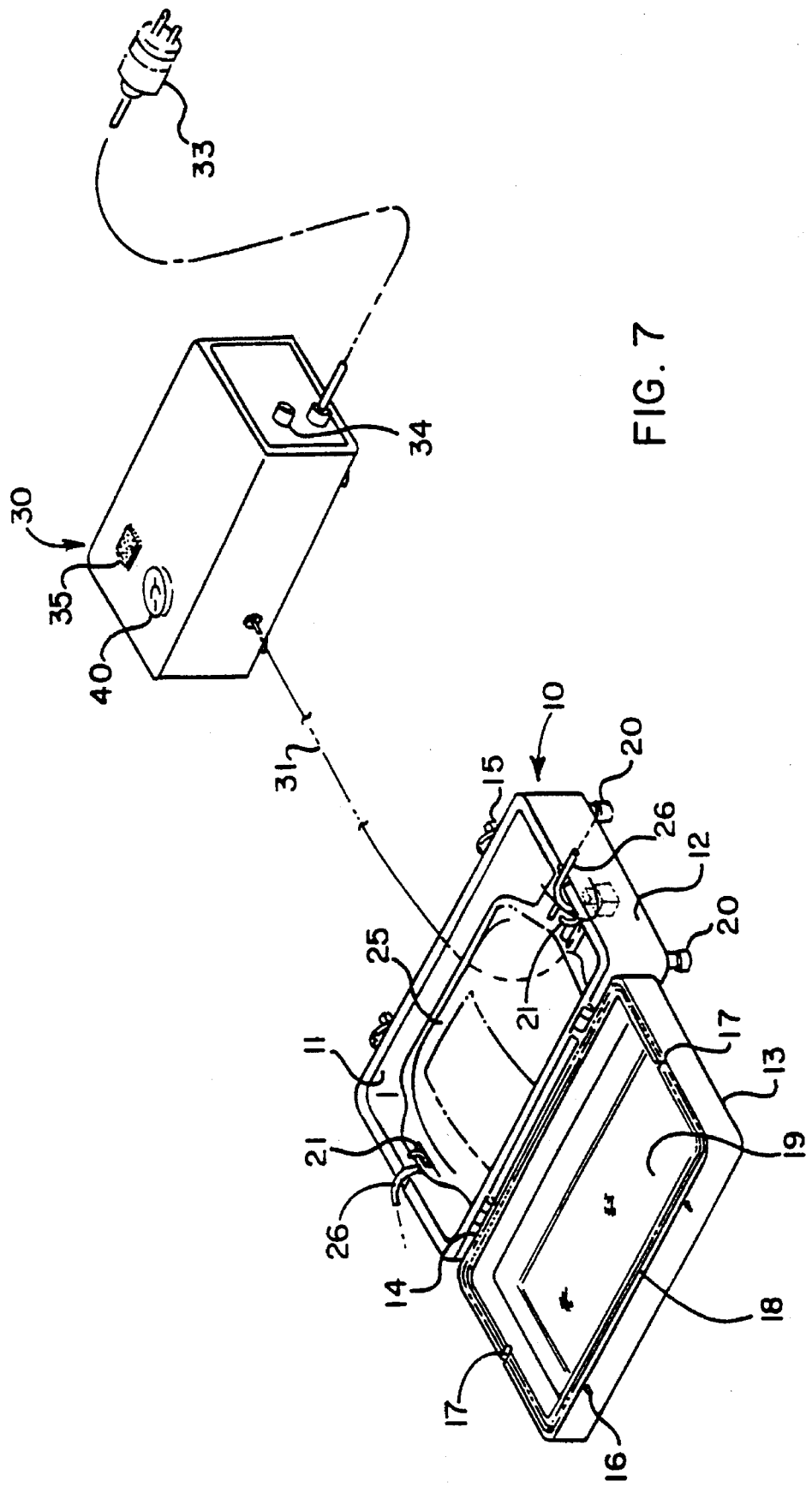
FIG. 7 is a perspective view of a second embodiment of an expressor according to the present invention.

To maintain a pressure differential between the chamber 11 and the exterior of the housing 10, the expressor preferably includes a sealing mechanism between the base 12 and the cover 13. For example, the sealing mechanism may include an elastomeric gasket 18, which may be disposed along the cover 13 where it interfaces with the base 12. The conduit opening 17 is preferably disposed so that the gasket 18 will create an air-tight seal around the conduit 26 as the cover 13 is sealed to the base 12. In the illustrated expressor only one conduit opening 17 is shown and it is disposed between the cover 13 and the base 12. Alternatively, the housing may have two or more openings to accommodate a plurality of conduits. For example, first and second openings on opposite sides of the housing could accommodate conduits extending from opposite ends of the fluid container, as shown in FIG. 7. Further, the openings on the housing may be disposed other than between the cover and the base, and an additional seal, such as an O-ring, may be used to seal the conduit to the housing.

The housing also preferably includes a transparent portion positioned to permit observation of the fluid container. For example, the transparent portion may be a window 19 in the cover 13. Alternatively, the entire housing by be formed from a transparent material such as a transparent plastic.

Figure 3:
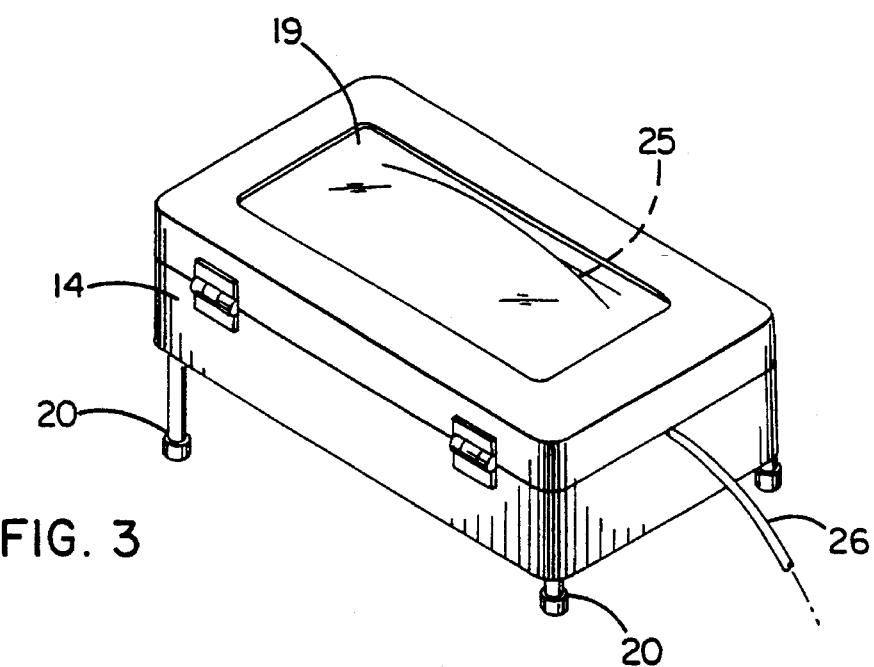
FIG. 3 is an enlarged perspective view of the housing of the embodiment of FIG. 1.

The housing 10 may further include a structure suitable for adjusting the orientation of the chamber 11. For example, the housing of the illustrated embodiment includes an adjustable leg 20 at each corner, and the legs 20 may be adjusted to orient the housing 11 in a horizontal position or in any desired tilted position. For example, it may be preferable to express air from the fluid container before any liquid is expressed. Consequently, as shown in FIG. 3, the legs 20 may be adjusted to tilt the chamber 11 so that the end of the fluid container 25 which communicates with the conduit 26 is higher than the opposite end of the container 25. One or more hooks 21 may be mounted inside the chamber 11 at the same end as the conduit opening 17 and/or at the end opposite from the conduit opening 17 to support the fluid container 25 when the housing 10 is tilted as shown in FIG. 3. In other words, the first and second hooks may be respectively located at first and second ends of the chamber and the container may be secured to the first and second hooks as shown in, for example, FIG. 7. As the housing is oscillated back and forth, the hooks restrict movement of the container within the chamber. Further, the housing 11 may be stood on the end opposite the conduit opening 17 or hung from either end when it is preferred to orient the housing in a vertical position.

The pressure regulating mechanism 30 may include any suitable pumping device 32 for supplying a fluid (i.e., either a liquid or a gas) to the chamber 11 of the housing 10 to elevate the pressure in the chamber 11 above the pressure within the container 25. In a preferred embodiment, the pumping device 32 is also capable of evacuating fluid from the chamber 11 to lower the pressure in the chamber 11 below the pressure within the container 25. By raising the pressure within the chamber 11, the volume of the fluid container 25 may be reduced and fluid (i.e., either a gas or a liquid) may be expressed from the fluid container. By lowering the pressure in the chamber 11, the volume of the fluid container 25 may be increased and fluid (i.e., either a gas or a liquid) may be drawn into the fluid container 25. The chamber 11 may be sized to limit expansion of the container 25 and thereby prevent the container from leaking or bursting. The absolute value of the difference between the chamber pressure and the pressure exterior to the housing may be relatively small, such as less than about 15 PSID.

Although the fluid supplied to and/or withdrawn from the chamber by the pressure regulating mechanism 30 may be a gas or a liquid, in a preferred embodiment, the fluid is ambient air. Air is convenient to handle and is readily available. Further, the air need not be sterile since it does not communicate with the interior of the fluid container 25. Devices for supplying and/or evacuating air from the chamber 11 are readily available. The suction and air pressure lines commonly available in many laboratories may also be used to evacuate or pressurize the housing.

Figure 4:
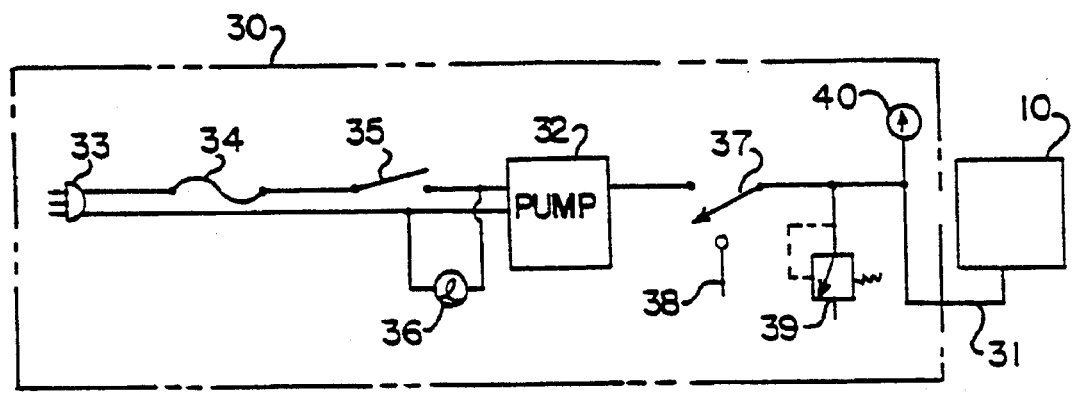
FIG. 4 is a block diagram of the embodiment of FIG. 1.

In the example illustrated in FIG. 4, the pumping device 32 is electrically operated and receives electrical power from an unillustrated power supply via a plug 33 connected to the pumping device 32 through a fuse 34 and a power switch 35 which can be opened and closed to switch the pumping device 32 on and off. An indicator light 36 may be connected to the power line so as to be illuminated when the power switch 35 is closed. The pumping device 32 may be connected to the hose 31 by a valve 37, which can be switched between a position in which the pumping device communicates with the hose 31 and a position in which the pumping device communicates with a vent 38. A pressure relief valve 39 may be disposed between the pumping device and the housing 10 to prevent pressure within the chamber 11 of the housing 10 from being greater than or less than a predetermined level. A pressure gauge 40 may be provided to visually indicate the current pressure in the chamber 11. Further, a control mechanism (not shown) may be coupled to the pumping device to increase or decrease the pressure by a predetermined amount or rate or to maintain the pressure at a predetermined level.

Figure 6:
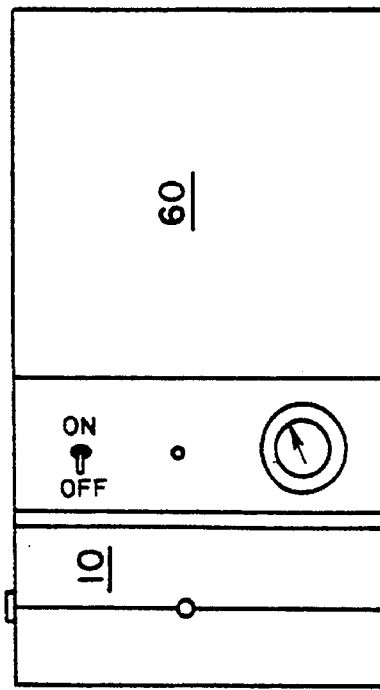
FIG. 6 is a top view of the embodiment of FIG. 5.
Figure 5:
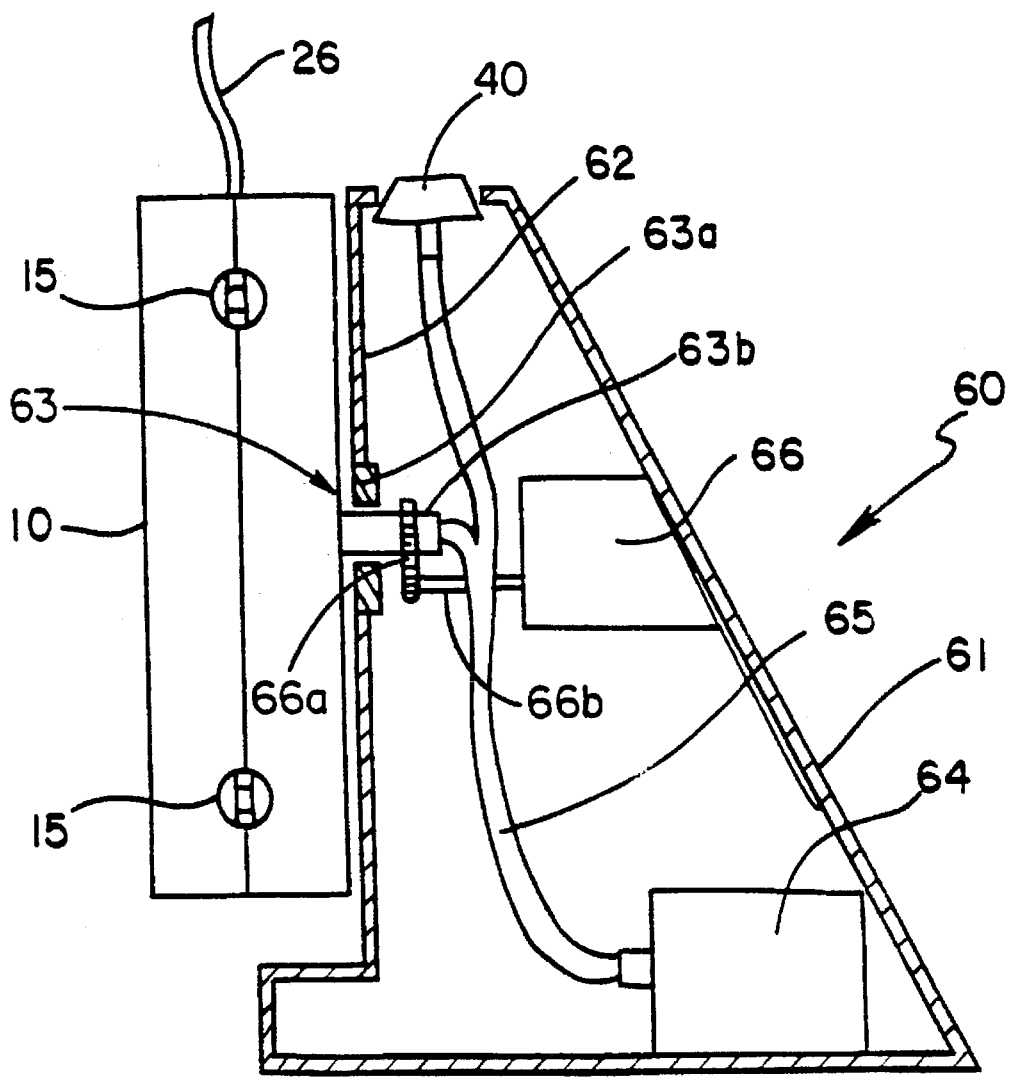
FIG. 5 is a partially cross-sectional side elevation of a second embodiment of an expressor according to the present invention.

The pressure regulating mechanism 30 and the housing 11 need not be coupled in the manner shown in FIG. 1. FIGS. 5 and 6 illustrate a second embodiment of the present invention in which a housing 10 and a pressure regulating mechanism 60 are configured as a single unit. The housing 10 of this embodiment is substantially identical to that of the previous embodiment, although the adjustable legs 20 may be omitted. The pressure regulating mechanism 60 includes a casing 61 having a support surface 62 which supports the housing 10 vertically. Although the support surface 62 is shown vertically fixed, it may be arranged to swing through a variety of angles and support the housing at any suitable angle from vertical through horizontal. The housing 10 can be permanently or detachably connected to the support surface 62 in any suitable manner. In the illustrated embodiment, the housing 10 is pivotably mounted on the support surface 62 by means of a swivel mount 63 comprising a bearing 63a secured to the support surface 62 and a hollow shaft 63b secured to the bottom surface of the housing 10 and rotatably supported by the bearing 63a. The casing 61 may be disposed about the housing 10 on at least two sides. For example, as shown in FIG. 5, the casing is disposed about the housing on a back side and a lower side. A stop (not shown) may be arranged to lock the housing in place once it has been swiveled to an appropriate position.

A pumping device 64 similar to the pumping device 32 of the first embodiment may be disposed inside the casing 61 and connected by a conduit, such as a hose 65, to the inside of the housing 10 and to a pressure gauge 40 mounted on the casing 61. The hose 65 can pass through the center of the hollow shaft 63b and connect to the housing 10 via a suitable fitting so that the housing can pivot about the axis of the pipe 63b without disturbing the hose 65. As shown in FIG. 6, controls and indicators for the pumping device 64 can be installed in the upper surface of the casing 61 for ease of use and observation. If agitation of the fluid in the container is desirable, a motor may be coupled to the housing in any suitable manner. For example, a motor 66 may be connected to the shaft 63b in order to oscillate the housing 10 axially along or circumferentially about the shaft 63b, thereby agitating the fluid in the container in the housing. The connection between the motor 66 and the shaft 63b may, for example, optionally include a mechanical arrangement such as an interlocking gearing arrangement 66a. The motor 66 may include a drive shaft 66b.

In a preferred mode of operation, the container 25, such as a flexible bag containing a biological fluid, is mounted to the base 12 of the housing 10 with the conduit 26 extending through the opening 17. The cover 13 is then sealed to the base 12 so that the container 25 is completely enclosed within and enveloped by the housing 10. The housing 10 is then oriented in a desired direction. For example, if the container 25 contains whole blood which has been centrifuged to form sediment and supernatant layers, the housing 10 is preferably oriented vertically. The conduit 26 may extend through the housing 10 from the lower end of the container 25, where the conduit 26 communicates directly with the sediment layer, or the conduit 26 may extend through the housing 10 from the upper end of the container 25, where the conduit 26 communicates directly with any air in the container 25 or with the supernatant layer.

With the housing 10 suitably oriented, fluid may be forced from or into the container 25 by supplying or withdrawing fluid from the chamber 11 of the housing 10 by means of the pressure regulating mechanism 30,60. For example, the pressure regulating mechanism 30,60 may supply ambient air into the chamber 11, increasing the pressure on the container 25. If the conduit 26 extends from the upper end of the container 25, the increase in pressure within the chamber 11 will first force any air and then the supernatant layer from the container 25 via the conduit 26. The interface between the supernatant layer and the sediment layer may be observed through the window 19 and it will rise as the supernatant layer is expressed from the container 25. Because it is frequently desirable to prevent the sediment layer from following the supernatant layer through the conduit 26, the pressurized fluid in the chamber 11 may be vented once the interface reaches the conduit 26, terminating flow through the conduit 17.

Figure 8:
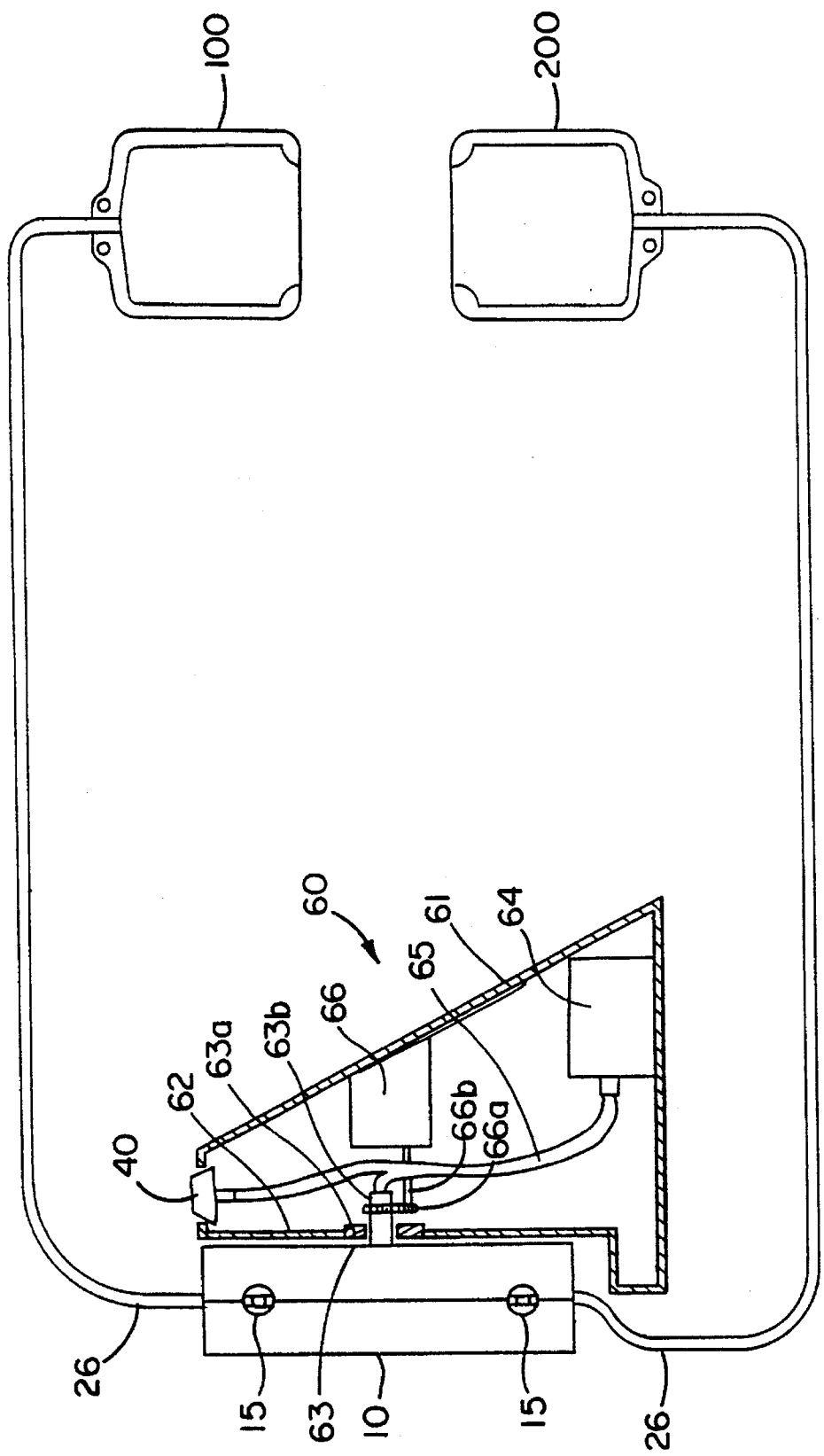
FIG. 8 is a perspective view of the second embodiment of the expressor illustrated in FIG. 7 connected to satellite collection containers.
Figure 9:
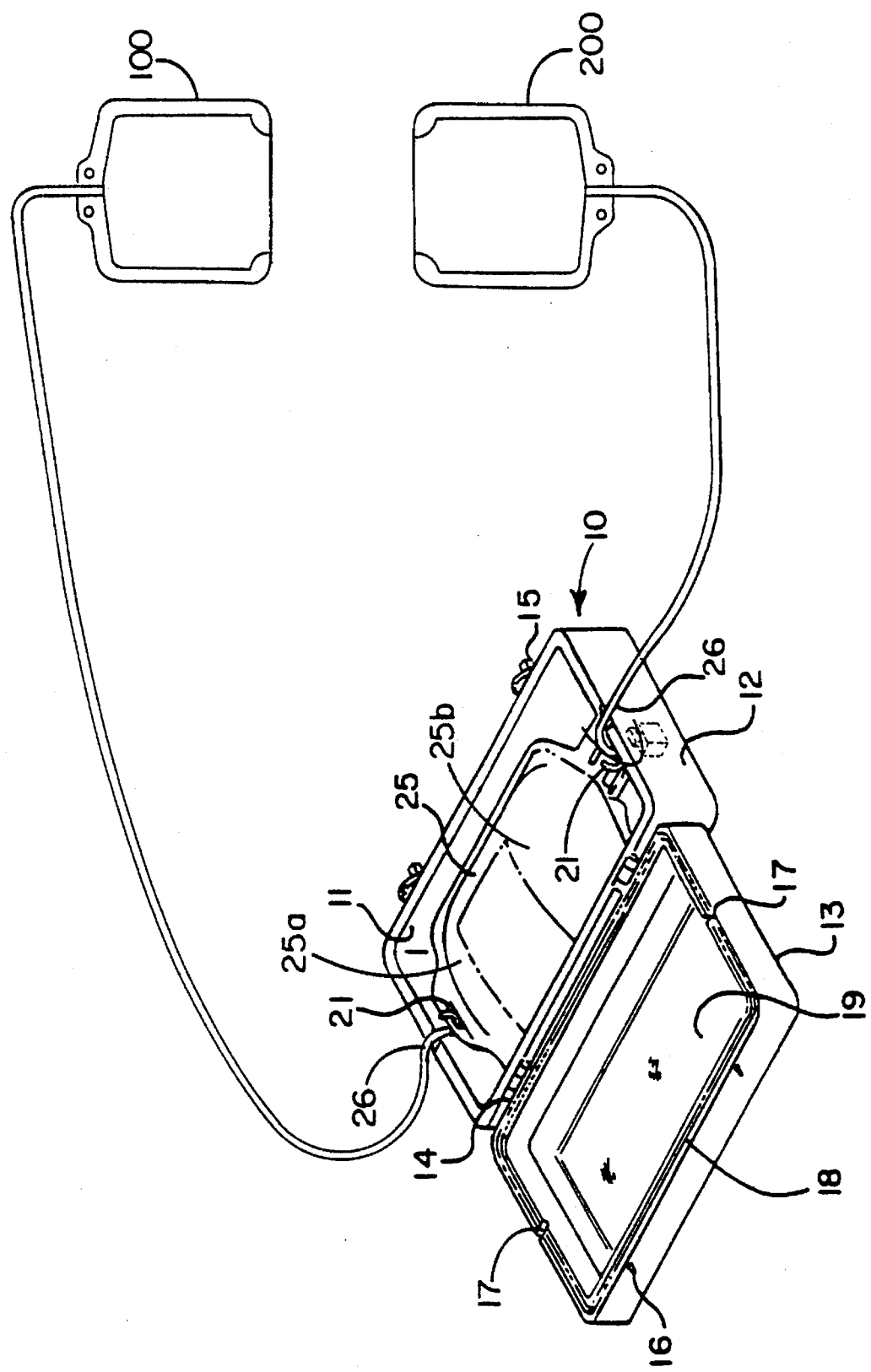
FIG. 9 is a detailed view of the flexible container connected to satellite collection containers.

FIG. 8 illustrates an exemplary embodiment of the expressor connected to two satellite containers or collection bags 100, 200, and FIG. 9 provides a more detailed illustration of the two satellite containers 100, 200 connected to the variable-volume container 25 within the housing 10. In the illustrated embodiment, one satellite container 100 is connected via conduit 26 to the flexible container 25 such that it is in communication with the supernatant layer 25a, and the second satellite container 200 is connected via conduit 26 to the flexible container 25 such that it is in communication with the sediment layers 25b. Alternatively, one of the two satellite containers 100, 200 may contain an additive as described previously.

The fluid pressure inside the chamber 11 of an expressor embodying the present invention will be substantially uniform throughout the chamber 11, so the outer surface of the fluid container 25 will be exposed to substantially uniform pressure. As a result, the fluid container 25 will be subjected to much less wrinkling, folding, or other forms of distortion than in conventional mechanical expressors or pressure cuffs. Because the fluid container 25 develops fewer wrinkles or folds and because fluid pressure is applied to the entire external surface of the fluid container 25, substantially all of the fluid in the fluid container 25 can be expressed from the container 25 rather than trapped in the folds and wrinkles. In addition, when the fluid container 25 contains centrifuged blood, the uniform external pressure applied to the fluid container 25 tends not to disturb the buffy coat interface. Further, the smaller amount of distortion of the fluid container 25 due to the uniform pressure and the absence of any structure such as a pressure cuff which can obstruct the view of an operator makes it much easier for the operator to visually determine the location of the buffy coat interface and to accurately control the transfer of fluid from the fluid container 25.

What is claimed is:

1. An expressor for varying the amount of fluid in a variable-volume container connected to at least one conduit, the expressor comprising:

a housing defining an enclosed chamber which can accommodate the container, the housing including at least one opening through which the conduit can extend, a base, a cover releasably mounted to the base, and at least one latch coupled to at least one of the base and cover;

a pressure regulating mechanism coupled to the housing to vary the pressure of fluid in the chamber and thereby vary the volume of the container, and wherein the latch includes a pressure equalization mechanism which equalizes the pressure between the chamber and the exterior of the housing before the cover is released from the base;

a casing; and an oscillating mechanism disposed within the casing and coupled to the housing via a shaft, the oscillating mechanism oscillating the housing circumferentially about the shaft, whereby the fluid in the container is agitated.

2. The expressor of claim 1 wherein the housing includes at least first and second openings oppositely disposed in the housing, wherein the fluid container includes first and second conduits respectively disposed in the first and second openings.

3. The expressor of claim 1 wherein the housing includes a transparent portion which is positioned to allow observation of the container.

4. The expressor of claim 1 including first and second securing mechanisms respectively located at first and second ends of the chamber and connectable to first and second ends of the variable-volume container, wherein the variable-volume container is removably fixed as the fluid is agitated.

5. The expressor of claim 4, wherein the first and second securing mechanisms respectively include first and second hooks.

6. The expressor of claim 1 wherein the pressure equalization mechanism includes a latch base and a pin, the latch base having an inner cam structure, an outer cam structure, and a track between the inner and outer cam structure, wherein when the base and the cover of the housing are engaged the pin engages the track.

7. The expressor of claim 1, wherein the shaft is hollow and includes a passage, and the pressure regulating mechanism is disposed in the casing and coupled to the housing via the passage in the hollow shaft.

8. The expressor of claim 7 wherein the at least one opening in the housing is disposed between the cover and the base, wherein the cover includes a transparent portion which is positioned to allow observation of the container, and wherein the housing includes securing mechanisms connectable to first and second ends of the variable-volume container, whereby the variable-volume container is removably fixed within the chamber as the fluid is agitated.

9. The expressor of claim 8 wherein the oscillating mechanism includes a motor and the shaft is coupled between the motor and the housing and rotatably disposed within a bearing mounted about the shaft.

10. The expressor of claim 8 wherein the bearing is mounted to the casing.

11. A method for processing a biological fluid comprising:

positioning a variable-volume container of biological fluid in an enclosed chamber of a housing with at least one conduit extending from the container to the exterior of the chamber;

securing the container at first and second ends of the enclosed chamber of the housing when the variable-volume container of biological fluid is positioned in the enclosed chamber;

varying the pressure within the chamber which is exerted on the container to vary the volume of the container and thereby force fluid out of or draw fluid into the container via the conduit, including supplying fluid to or withdrawing fluid from the chamber by a pressure regulating mechanism coupled to the chamber; and rotating a shaft coupled between a motor and the housing and disposed within a bearing mounted about the shaft, including agitating the fluid in the container by moving the housing back and forth in an oscillatory fashion.

12. The method of claim 11 further comprising equalizing the pressure between the chamber and the exterior of the housing before removing the container from the housing.

13. The method of claim 12 wherein equalizing the pressure includes operating a latch which connects a cover of the housing to a base of the housing.

14. An expressor for varying the amount of fluid in a variable-volume container connected to at least one conduit, the expressor comprising:

a housing including a base and a cover coupled to the base, and defining an enclosed chamber which can accommodate the container, the housing having at least one opening formed between the base and the cover through which the conduit can extend;

a casing including an opening;

a pressure regulating mechanism, disposed within the casing and coupled to the housing to vary the pressure of fluid in the chamber and thereby vary the volume of the container;

a bearing disposed about the opening;

a motor disposed within the casing; and a shaft coupled between the housing and the motor and supported by the bearing and connected to the housing at a first end, the shaft oscillating the housing in response to actuation of the motor, whereby fluid in the container is agitated.

15. The expressor of claim 14 wherein the container pivots about the shaft.

16. The expressor of claim 14 wherein the container is oscillated circumferentially back and forth with the shaft.

17. The expressor of claim 14 wherein the shaft is hollow and includes a passage and wherein the pressure regulating mechanism is coupled to the chamber through the passage.

18. The expressor of claim 14 wherein the housing includes at least first and second openings oppositely disposed in the housing wherein the container includes first and second conduits respectively disposed in the first and second openings.

19. The expressor of claim 14 wherein the housing includes a transparent portion which is positioned to allow observation of the container.

20. The expressor of claim 14 wherein the housing includes first and second securing mechanisms located at first and second ends of the chamber and connectable to first and second ends of the variable-volume container, wherein the variable-volume container is removably fixed as the fluid is agitated.

21. An expressor for varying the amount of fluid in a variable-volume container connected to at least one conduit, the expressor comprising:

a housing defining an enclosed chamber which can accommodate the container, the housing having at least one opening through which the conduit can extend;

a pressure regulating mechanism coupled to the housing to vary the pressure of fluid in the chamber and thereby vary the volume of the container;

a motor coupled to the housing to oscillate the container and to agitate fluid in the container; and a hollow shaft having a passage, the hollow shaft being coupled to the motor and transferring movement from the motor to the container and wherein the pressure regulating mechanism is coupled to the chamber through the passage.

22. The expressor of claim 21 wherein the housing includes at least first and second openings through which first and second conduits connected to the variable-volume container can extend.

23. The expressor of claim 21 including first and second securing mechanisms located at first and second ends of the chamber and connectable to first and second ends of the variable-volume container, wherein the variable-volume container is removably fixed as the fluid is agitated.

24. The expressor of claim 23, wherein the first and second securing mechanisms respectively include first and second hooks.

25. The expressor of claim 21, wherein the housing further includes a base, a cover releasably mounted to the base, and at least one latch coupled to at least one of the base and cover, the latch includes a pressure equalization mechanism which equalizes the pressure between the chamber and the exterior of the housing before the cover is released from the base.

26. The expressor of claim 25 wherein the pressure equalization mechanism includes a latch base and a pin, the latch base having an inner cam structure, an outer cam structure, and a track between the inner and outer cam structure, wherein when the base and the cover of the housing are engaged the pin engages the track.

27. The expressor of claim 21, wherein the housing includes a transparent portion which is positioned to allow observation of the container.

28. A method for processing a biological fluid including blood or a blood product comprising:

placing a variable-volume container of the biological fluid into an enclosed chamber of an expressor housing;

varying the pressure within the enclosed chamber, responsive to a control mechanism, to establish a flow of the biological fluid between the variable-volume container and an additional container, wherein the pressure is varied by at least one of supplying and evacuating a fluid via a passage through a hollow shaft coupling a pressure regulating mechanism to the enclosed chamber; and agitating the biological fluid in the variable-volume container by moving the expressor housing back and forth in a oscillatory fashion utilizing a motor coupled to the expressor housing through the hollow shaft.

29. The method of claim 28 wherein varying the pressure includes establishing a flow of the biological fluid out of the variable-volume container and into the additional container, and establishing fluid flow into the variable-volume container from the additional container.

30. The method of claim 28 further comprising equalizing the pressure between the chamber and the exterior of the expressor housing before removing the container from the chamber.

31. The method of claim 30 wherein equalizing the pressure includes operating a latch which connects a cover of the expressor housing to a base of the expressor housing.

32. A method for processing blood or a blood product comprising:

positioning a variable-volume container of blood or a blood product in an enclosed chamber of a housing having a base and a cover;

securing the container at first and second ends of the chamber as the variable-volume container is positioned in the enclosed chamber;

varying the pressure within the chamber to vary the volume of the container and thereby force the blood or the blood component out of the variable-volume container into an additional container, or thereby draw fluid from the additional container into the variable volume container;

moving the blood or the blood product within the variable-volume container by moving the chamber in an oscillatory fashion; and equalizing the pressure between the chamber and the exterior of the housing before removing the container from the housing, including operating a latch which connects the cover of the housing to a base of the housing.

33. The method of claim 32 wherein varying pressure within the chamber establishes the flow of an additive solution from the additional container into the variable-volume container.

34. The method of claim 32 wherein moving the blood or blood product includes rotating a shaft coupled between a motor and the housing and disposed within a bearing mounted about the shaft.

35. A method for transporting a biological fluid between first and second interconnected flexible containers through tubing comprising:

placing one of the first and second interconnected flexible containers into an enclosed chamber of a housing;

securing at least one of the first and second interconnected flexible containers at first and second ends within the enclosed chamber of the housing;

varying the pressure within the chamber to establish a flow of biological fluid between the first and second interconnected flexible containers, including supplying fluid to or withdrawing fluid from the chamber by a pressure regulating mechanism coupled to the chamber; and agitating the biological fluid in one of the first and second flexible containers placed in the enclosed chamber by moving the housing back and forth in an oscillatory fashion utilizing a motor coupled to the housing through a hollow shaft, the hollow shaft having a passage through which the pressure regulating mechanism is coupled to the chamber.

36. The method of claim 35 including varying the pressure responsive to a control mechanism.

37. The method of claim 36 wherein varying the pressure includes varying the pressure by a predetermined amount or at a predetermined rate.

38. The method of claim 36 wherein varying the pressure includes maintaining the pressure at a predetermined level.

39. The method of claim 35 wherein varying the pressure within the chamber establishes the flow of an additive solution between the first and second interconnected flexible containers.

40. The method of claim 35 wherein transporting the biological fluid includes transporting blood or a blood product.

41. The method of claim 35 further comprising equalizing the pressure between the chamber and the exterior of the housing before removing one of the first and second interconnected flexible containers from the chamber.

42. The method of claim 41 wherein equalizing the pressure includes operating a latch which connects a cover of the housing to a base of the housing.

43. The method of claim 42 including orienting the at least one of the first and second interconnected flexible containers for transporting one of supernatant and sediment layers of centrifuged whole blood.

44. The method of claim 43 wherein orienting includes orienting the at least one of the first and second interconnected flexible containers so that the tubing is in fluid communication with the sediment layer.

45. The method of claim 43 wherein orienting includes orienting the at least one of the first and second interconnected flexible containers so that the tubing is in fluid communication with the supernatant layer.

46. The method of claim 35 wherein agitating the biological fluid includes moving the enclosed chamber back and forth about a fixed point.

47. The method of claim 35 wherein agitating the biological fluid includes moving at least one of the first and second interconnected flexible containers circumferentially.

48. The method of claim 35, including monitoring the fluid transport through a transparent section of the housing.

49. The method of claim 35 wherein securing includes respectively coupling first and second ends of the at least one of the first and second interconnected flexible containers with first and second securing mechanisms.

50. The method of claim 35 wherein securing includes coupling first and second hooks to first and second ends of the at least one of the first and second interconnected flexible containers.

51. The method of claim 35 wherein transporting the biological fluid includes transporting the biological fluid from the first interconnected flexible container into the second interconnected flexible container and transporting the biological fluid from the second interconnected flexible container into the first interconnected flexible container.

52. The method of claim 35 wherein transporting the biological fluid includes transporting the biological fluid from one or more sterile blood collection bags.

53. An expressor for varying the amount of fluid in a variable-volume container connected to at least one conduit, the expressor comprising:

a housing defining an enclosed chamber which can accommodate the container, the housing having at least one opening through which the conduit can extend;

a pressure regulating mechanism coupled to the housing to vary the pressure of fluid in the chamber and thereby vary the volume of the container;

a casing;

an oscillating mechanism disposed within the casing and coupled to the housing via a shaft, the oscillating mechanism oscillating the housing circumferentially about the shaft, whereby the fluid in the container is agitated; and securing mechanisms respectively located at first and second ends of the chamber and removably connectable to first and second ends of the variable-volume container, wherein the variable-volume container is removably fixed as the fluid is agitated thereby restricting movement of the container within the enclosed chamber.

* * * * *